US005654335A

United States Patent [19]
Schoenwald et al.

[11] Patent Number: 5,654,335
[45] Date of Patent: Aug. 5, 1997

[54] TOPICAL USE OF ETHYL ETHACRYNATE FOR GLAUCOMA TREATMENT

[75] Inventors: Ronald D. Schoenwald; Charles F. Barfknecht, both of Iowa City, Iowa

[73] Assignee: University of Iowa Research Foundation, Iowa City, Iowa

[21] Appl. No.: 605,927

[22] Filed: Feb. 23, 1996

[51] Int. Cl.⁶ .................................................. A01N 37/02
[52] U.S. Cl. .................................... 514/543; 514/545
[58] Field of Search ................................ 514/543, 545

[56] References Cited

U.S. PATENT DOCUMENTS

| | | | |
|---|---|---|---|
| 3,478,085 | 11/1969 | Cragoe, Jr. | 560/53 |
| 4,731,381 | 3/1988 | Abraham et al. | 514/571 |
| 4,731,473 | 3/1988 | Abraham et al. | 562/464 |
| 4,757,089 | 7/1988 | Epstein | 514/571 |
| 4,855,289 | 8/1989 | Wester et al. | 514/171 |
| 5,244,922 | 9/1993 | Burzynski | 514/561 |
| 5,306,731 | 4/1994 | Epstein | 514/562 |
| 5,352,702 | 10/1994 | Cyrlin | 514/571 |
| 5,395,847 | 3/1995 | Weinstock et al. | 514/397 |
| 5,424,450 | 6/1995 | Boswell et al. | 548/253 |
| 5,458,883 | 10/1995 | Epstein | 424/427 |
| 5,472,706 | 12/1995 | Friedman et al. | 424/450 |
| 5,506,226 | 4/1996 | May | 514/211 |
| 5,565,434 | 10/1996 | Barfknecht et al. | 514/25 |
| 5,585,401 | 12/1996 | Brandt et al. | 514/562 |

FOREIGN PATENT DOCUMENTS 1545601  11/1968  France.

OTHER PUBLICATIONS

Wang et al., Arch Ophthalmol/vol. 112, Mar. 1994, pp. 390–394.

Tingey et al., Arch Ophthalmol/vol. 110, May 1992, pp. 699–702.

Johnson et al., Current Eye Research/vol. 12 No. 5 1993, 385–396.

Cynkowska et al., Abstract PDD 7145, American Association of Pharmaceutical Scientists, Nov. 1995, p. S–229.

Melamed et al., Abstract of Association Meeting, Association for Research in Vision Ophthalmology (ARVO), (1992).

*Primary Examiner*—Jeffrey C. Mullis
*Attorney, Agent, or Firm*—Zarley, McKee, Thomte, Voorhees & Sease

[57] ABSTRACT

A method of reducing intraocular eye pressure by topically applying to an affected eye a small but therapeutically effective intraocular eye pressure reducing amount of the compound ethyl ethacrynate.

7 Claims, No Drawings

TOPICAL USE OF ETHYL ETHACRYNATE FOR GLAUCOMA TREATMENT

BACKGROUND OF THE INVENTION

Glaucoma, which some estimate affects 2 million adults over 40, is an impairment of vision caused by too much fluid pressure within the eye.

Surgical treatment for glaucoma is effective; however, it is expensive, and some surgeons will use surgery only as a last resort.

Glaucoma stems from an excess of fluid behind the cornea, the three-layered tissue that acts as a window to let light enter. Fluid-carrying nutrients, such as potassium and glucose, constantly wash the inside of the cornea to keep it healthy, much as tears wash the outside of the cornea.

In some middle-aged adults, fluids build up faster than can be absorbed back into the blood for one of two reasons: the ciliary body (a tiny tissue behind the iris) may excrete too much fluid, or the fluid may not drain off at the normal rate.

Either way, the excess fluid damages the optic nerve. At first a glaucoma victim usually experiences a subtle loss of peripheral vision—objects will seem to disappear from certain spots to the side. But glaucoma often leads to middle-age blindness.

Unfortunately, the two approaches to general drug usage in treating glaucoma—topical (dropped into the eye) and oral (through the mouth)—each have a peculiar set of side effects.

To make the long journey, oral drugs must be dosed in very high concentration. One class of drugs, called carbonic anhydrase inhibitors, slow the formation of fluid by inhibiting a chemical reaction at the ciliary body. Along with their well-tested effectiveness comes nausea, tingling in fingers and toes, and other side effects. Oral drugs generally do not, however, cause side effects in the eye, but the systemic delivery system is slow and causes other side effects.

From the above discussion it can be seen that there is a continuing need for the development of new drugs that can be applied topically in order to avoid systemic effects, and which may at the same time still be highly effective. This, of course, necessitates that the compound be one which will, first of all, effectively evoke a response which will provide the correct intraocular pressure, and secondly, penetrate the cornea rapidly and distribute well to the active site, i.e. ciliary body of the eye, or perhaps the trabecular meshwork. It goes without saying that compounds which are active as intraocular pressure inhibitors, but have limited penetrability across the cornea and to the site of activity are, as a practical matter, of limited value in developing truly effective topical glaucoma treatments, even though they may have some test activity in vitro, i.e. in a test tube. Put another way, if the compound does not have the correct distribution and penetration properties, its chances of being pharmacologically active, when topically applied to an affected eye in patients, are small at best. Thus, it is important if one is developing effective topical medicaments, that they be active in vitro, and that they be active when actually applied to an affected eye from the standpoint of penetrating the cornea and reaching the active site for effective treatment of glaucoma. There has been some work in the past with ethacrynic acid, but it has not proven effective in human models, even though it may have good pharmacological activity.

Accordingly, it is a primary object of the present invention to provide a new, highly effective topical treatment for glaucoma that has a surprisingly fast rate of absorption in comparison with ethacrynic acid, coupled with a demonstrated lack of toxicity risk and in vivo effectiveness.

It is another objective of the present invention to provide a new composition and new treatment using ethyl ethacrynate for glaucoma that can be used topically to avoid many of the undesirable side effects of other currently available treatments.

The method and manner of accomplishing each of the above objectives, as well as others, will become apparent from the detailed description of the invention which follows hereinafter.

SUMMARY OF THE INVENTION

Ethyl ethacrynate is used as an effective topical glaucoma treatment agent. It surprisingly is active with a high rate of absorption across the corneal tissue, even though closely-related structures, such as methyl and propel ester structures of ethacrynic acid, are not active.

DETAILED DESCRIPTION OF THE INVENTION

Ethyl ethacrynate has the following formula:

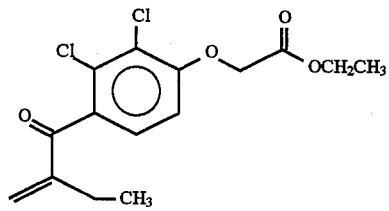

This is a known ester of ethacrynic acid, previously reported as a diuretic, but previously unreported as a topical treatment for glaucoma. This compound demonstrates an unexpected topical effectiveness in the ethyl ester form for glaucoma treatment, especially when neither the methyl ester nor the propyl ester are active topically for treating agents for glaucoma. It is not known precisely why the ethyl ester of ethacrynic acid is topically active for glaucoma treatment, whereas the very closely related methyl and propyl esters are not. While applicant does not wish to be bound by any theory of operability, it is believed that the ethyl ester has the proper combination of absorption rate of the prodrug and cleavage to the active species, ethacrynic acid, which exerts the potent therapeutic effect. The methyl and the normal propyl esters somehow fail to achieve this proper combination. Applicant relies upon the simple fact that this compound does work topically for a glaucoma-treating agent, whereas the most closely related compounds simply do not, as evidence of unexpected result.

In conjunction with the evaluation of the present invention and its unexpected results, it is important to distinguish between topical application for treating glaucoma and oral dosing for treating glaucoma. This has been mentioned previously, but it is emphasized here again that topical application (dropped into the eye) has the significant advantage of avoiding most of the systemic side effects, but for effectiveness it is essential that the compound or compounds be actively transported across the cornea at sufficient levels to reach the proper receptor site. Thus, topically active compounds must have the correct distribution and penetration properties. Ethacrynic acid, and most of its ester analogues, while perhaps having some activity in oral administration, do not exhibit such activity topically. In this respect, ethyl ethacrynate appears to be peculiarly unique in that it has highly effective pharmacological properties, and at the same time is topically active.

Typically, the method of administration is simply preparing an ointment (such as petrolatum) or gel with a conventional pharmaceutical carrier (such as carbopol) and topically administering the gel composition. The amount of active use in the composition should be from about 0.25% by weight to about 5% by weight for an eye drop composition, preferably from about 0.5% by weight to about 2.0% by weight. The important point is not the dose amount, but simply that it be an amount that is effective in treating glaucoma and yet not be so strong as to provide eye irritation or side effects. Generally, amounts within the ranges herein specified are satisfactory.

Assuming a stable ester analogue, the carrier for the eye drop composition may be an isotonic eye treatment carrier buffered to a pH of from about 4 to about 8, and typically it will contain small amounts of conventional wetting agents and anti-bacterial agents. The preferred pH is within the range of from about 6.8 to about 7.8 and contains sufficient sodium chloride or equivalent to be isotonic. Anti-bacterial agents where the are included may be within the range of from about 0.004% (W/V) to about 0.02% (W/V) of the composition.

The ophthalmically active compounds may be incorporated into various ophthalmic gel formulations for delivery to the eye. In order to form sterile ophthalmic ointment formulations, the active ingredient is combined with a preservative in an appropriate vehicle, such as mineral oil, liquid lanolin, or white petrolatum. Sterile ophthalmic gel formulations may be prepared by suspending the active nonsteroidal drugs of this invention in a hydrophilic base prepared from a combination of carbopol −940 (a carboxy vinyl polymer available from the B. F. Goodrich Company) according to published formulations for analogous ophthalmic preparations. Preservatives and tonicity agents can also be incorporated.

EXAMPLES

The following examples are offered to illustrate the preparation of the ethyl ester of ethacrynic acid and its effective use topically.

1,3-Dicyclohexylcarbodiimide (1.2 equivalents) and 1-hydroxybenzotriazole (1.2 equivalents) were combined in 30 ml. of dry tetrahydrofuran (THF). Ethacrynic acid (1.0 equivalent) was dissolved in 10 ml. of hot THF and added to the stirred solution over a five-minute period. Anhydrous ethanol (1.0 equivalent) was added, and the reaction mixture was stirred overnight. The solids were removed by paper filtration and the solvents removed in vacuo. After the addition of 20 ml. of diethyl ether, the solution was extracted with 2% aqueous acetic acid (10 ml.), with 3% aqueous sodium bicarbonate (twice with 10 ml.), and water (20 ml.). The diethyl ether solution was dried over sodium sulfate, filtered through paper, and passed through a short silica gel column. Removal of the solvent yielded the product as a liquid which possessed proton nuclear magnetic resonance spectra, electron impact mass spectra, and combustion analysis of carbon, hydrogen, and nitrogen consistent with assigned structure.

The recovered ethyl ester of ethacrynic acid was used topically as described below in an "IOP recovery rate assay" analysis.

The "IOP recovery rate assay", as reported by Vareilles and Lotti (Ophthal. Res., 13, 72–79, 1981), was used. In this assay 20% sodium chloride solution was infused into the marginal ear vein of New Zealand White rabbits for 10 minutes at a rate of 1 mL/min (N=12). IOP was measured at 15, 25, 35, 45, 60, 75, 90 and 120 minutes with an applanation pneumatonometer (Alcon Digilab Model D). Fifty μL of a 2% solution or suspension of new drug agents containing a pH 7.4 phosphate buffer was administered topically to the right eye 60 minutes before the start of the sodium chloride infusion. Control animals were given vehicle without drug.

The average (± standard deviation) slope values for 10–12 rabbit eyes were as shown in Table I.

TABLE I

| TEST COMPOUND | Avg. Drug Treated Rabbits (slope) | Avg. Blank Treated Rabbits (slope) | % Decrease in Slope |
|---|---|---|---|
| Ethacrynic acid | 0.0673 ± 0.0179 | 0.0752 ± 0.0176 | 10.5 |
| Ethyl Ethacrynate | 0.0520 ± 0.0354 | 0.0804 ± 0.0317 | 35.4 |

The hypertonic sodium chloride solution causes a temporary decline in IOP which returns to normal IOP in about 90 minutes if no drug is administered. IOP gradually returns to normal at a constant rate, but more slowly if the in vivo secretion rate of aqueous humor is reduced due to the presence of drug. The return to normal IOP is measured from the positive linear slope, which is a measure of the constant rate of return to normal IOP, and begins at about 30–45 minutes after starting the NaCl infusion. A comparison of the slope with and without the addition of test agent to the rabbit eye is expressed as "% decrease in slope".

From the above tests, it can be seen that the ethyl ethacrynate was effective in comparison with ethacrynic acid compound which had previously been reported as active in an animal model, but recently failed in human trials. Much greater penetration ability of ethyl ethacrynate indicates that in spite of recent failed tests in human models for ethacrynic acid, ethyl ethacrynate would be effective. Moreover, surprisingly similar tests on the methyl and propyl esters of ethacrynic acid showed them to be ineffective and of no particular value topically.

It therefore can be seen that the invention accomplishes at least all of its stated objectives.

What is claimed is:

1. A method of reducing intraocular eye pressure, said method comprising:

topically applying to an affected eye a small but therapeutically effective intraocular eye pressure reducing amount of ethyl ethacrynate.

2. The method of claim 1 wherein the active ethyl ethacrynate is dosed from an eye drop composition containing from about 0.25% by weight to about 5% by weight of the active in the eye drop composition.

3. The method of claim 1 wherein the eye delivery composition is an ointment composition either aqueous or oleaginous.

4. The method of claim 2 wherein the dose amount is from about 0.5% by weight to about 2% by weight of said composition.

5. An isotonic eye ointment treatment composition which comprises:

an ointment suspension of a small but therapeutically effective intraocular eye pressure reducing amount of the compound ethyl ethacrynate in a pharmaceutically acceptable ointment carrier.

6. The composition of claim 5 wherein the amount of ethyl ethacrynate in the ointment composition is from about 0.25% by weight to about 5% by weight of the eye ointment composition.

7. The composition of claim 6 wherein the dose amount is from about 0.5% by weight to about 2% by weight of said ointment composition.

* * * * *